United States Patent [19]

Buchler et al.

[11] Patent Number: 4,973,718

[45] Date of Patent: * Nov. 27, 1990

[54] METHOD FOR THE CATALYTIC EPOXIDATION OF OLEFINS WITH HYDROGEN PEROXIDE

[75] Inventors: Johann Buchler, Darmstadt; Manfred Schmidt, both of Gelnhausen; Guenter Prescher, Larchmont, N.Y.

[73] Assignee: Degussa Aktiengesellschaft, Frankford am Main, Fed. Rep. of Germany

[*] Notice: The portion of the term of this patent subsequent to Jul. 4, 2006 has been disclaimed.

[21] Appl. No.: 247,300

[22] Filed: Sep. 21, 1988

[30] Foreign Application Priority Data

Sep. 21, 1987 [DE] Fed. Rep. of Germany ....... 3731690

[51] Int. Cl.$^5$ ............................................ C07D 301/12
[52] U.S. Cl. ..................... 549/531; 540/145
[58] Field of Search ........................ 549/531; 540/145

[56] References Cited

U.S. PATENT DOCUMENTS

| | | | |
|---|---|---|---|
| 3,778,451 | 12/1973 | Poite | 549/531 |
| 4,418,203 | 11/1983 | Kim | 549/531 |
| 4,822,899 | 4/1989 | Groves et al. | 549/533 |
| 4,845,252 | 7/1989 | Schmidt et al. | 549/531 |

OTHER PUBLICATIONS

Kruppa Dissertation, Technischen Hochschule Darmstadt, 1989.

Sheldon, "Synthetic and Mechanical Aspects of Metal Catalyzed Epoxidations with Hydroperoxides", Journal of Molecular Catalysis, vol. 7, 1960, pp. 107–126.

Harriman et al., "Redox Reactions of Osmium Porphyrins", Journal Chem. Soc., Dalton Trans., 1988, pp. 2705–2711.

Hrung et al., "Salt-Type Complexes of Porphyrins: Monocations Octaethyl Porphinium Tri-Microhalogenohexacarbonyldirbenate (I)", Journ. of American Chemical Society, vol. 98-24, Nov. 1976, pp. 7878–7880.

Primary Examiner—Glennon H. Hollrah
Assistant Examiner—Ba K. Trinh
Attorney, Agent, or Firm—Beveridge, DeGrandi & Weilacher

[57] ABSTRACT

A method for the catalytic epoxidation of olefins with hydrogen peroxide in the presence of rhenium-oxo-complexes or of a binuclear compound of the type μ-oxobis [porphyrinato-oxo-rhenium(V)] with octaethyl porphyrin or 5,10,15,20-tetraphenyl porphyrin or 5,10,15,20-tetra(4-pyridyl)-porphyrin as ligands.

13 Claims, No Drawings

METHOD FOR THE CATALYTIC EPOXIDATION OF OLEFINS WITH HYDROGEN PEROXIDE

Introduction and Background

The present invention relates to a method for the catalytic epoxidation of olefins with hydrogen peroxide in the presence of a transitional metal porphyrin complex in which a required charge equalization takes place by an anion.

Olefin oxides (oxiranes) are compounds of considerable industrial significance. They are used in the area of varnishes, for the preparation of polyethers, polyurethanes, epoxide resins, detergents, glycols and a plurality of organic intermediate products (cf. U.S. Pat. No. 2,412,136 and DE-AS No. 11 39 477).

Various methods are already known for the epoxidation of olefins. Thus, for example, oxiranes can be prepared according to the chlorohydrin method by reacting olefins with chlorine or sodium hypochlorite in alkaline medium and by a subsequent treatment with bases. A fundamental disadvantage of this method arises because of the formation of saline waste water and undesirable, chlorinated byproducts which are harmful to the environment (cf. "Ullmann's Enzyklopädie der technischen Chemie"[Ullmann's Encyclopedia of Industrial Chemistry], vol. 10, p. 565, (3d edition)).

Another known process is based on the reaction of olefins with organic hydroperoxides in the presence of a catalyst (cf. DE-AS No. 14 68 012). This second synthetic method has the decisive disadvantage that as a result of the stoichiometry of the epoxidation reaction, the normally expensive, organic hydroperoxide (ROOH, in which R can signify e.g. a low-molecular group such as t-butyl or cumyl) is converted into large amounts of the corresponding alcohol (ROH) during the reaction according to equation:

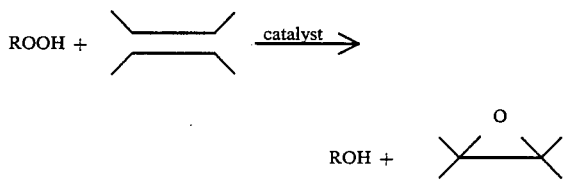

If the corresponding alcohol can not be utilized, it must be separated from the method product and disposed of or converted back into the corresponding hydroperoxide via several method steps, which makes the epoxidation method expensive in an economic sense too.

Another known method is based on the use of organic peracids which are obtained by means of oxidation by air of the corresponding aldehydes or from carboxylic acids with hydrogen peroxide (cf. BE-PS No. 535 068). The use of these organic percarboxylic acids is always associated with a risk on account of their decomposability and therefore requires expensive precautionary measures as regards carrying out the method and in respect of equipment design. In addition, large amounts of the corresponding carboxylic acids are always created in epoxidations with organic peracids which amounts must be separated in a stoichiometric or more than stoichiometric amount and disposed of or returned.

The described disadvantages can be eliminated by using hydrogen peroxide as epoxidation agent since in this instance according to theory only water should accumulate along with the epoxidation product. Since the reactivity of hydrogen peroxide is weak in relation to olefins, epoxidations with this reagent are carried out with the use of catalysts. Catalysts such as molybdenum compounds and tungsten compounds are suitable only for a few olefins. Note in this connection, for example, the following prior developments: GB No. 837,464, in which the various metal catalysts described in "J.A.C.S.", vol. 59, pp. 2342 to 2344, 1937 are used; U.S. Pat. No. 2,786,854, according to which tungstic acid is used; U.S. Pat. No. 2,833 787, according to which acidic salts of metals of group VI of the periodic system of the elements, e.g. of tungsten or molybdenum., are used; BE-PS NO. 860,776, according to which compounds containing tungsten and containing molybdenum are used; U.S. Pat. No. 3,993,673, according to which catalysts containing arsenic are used; U.S. Pat. No. 3,953,362, according to which a catalyst containing molybdenum is used; U.S. Pat. No. 4,026,908, according to which mercury derivatives plus a compound with molybdenum, tungsten, vanadium or titanium is used; U.S. Pat. No. 3,806,467, according to which organic and inorganic tin compounds plus organic or inorganic compounds containing molybdenum, tungsten, vanadium, selenium or boron are used; "Bull. Chem. Soc. Jap." 42, pp. 1604, 1969, according to which selenium dioxide is used; and U.S. Pat. No. 3,778,451, according to which compounds with molybdenum, tungsten, vanadium, niobium, tantalum, uranium and rhenium are used.

These above mentioned substances are catalytically active; however, the methods which can fundamentally be carried out with them have not found acceptance in the art for various reasons. In conjunction with hydrogen peroxide solutions, either the hydrogen peroxide is rapidly decomposed by them or only an unsatisfactory epoxidation speed is achieved. Methods with these catalysts are also problematic to the extent that in addition to the desired epoxidation product, frequently rather large amounts of byproducts such as diols and ketones are formed whose separation can pose considerable problems.

Attempts have also already been undertaken to carry out methods for the catalytic epoxidation of olefins with other epoxidation agents using metal porphyrin complexes as catalysts. Compounds such as iodosobenzene (PhIO) (J. T. Groves; T. E. Nemo; R. S. Myers, "J. Am. Chem. Soc.", 101, 1032, 1979; alkali metal hypochlorite such as NaOCl or LiOCl (E. Guilmet; B. Meunier, "Tetrahedron Lett." 1980, 4449) as well as organic hydroperoxides such as t-butyl hydroperoxide or cumol hydroperoxide (H. J. Ledon; P. Durbut; F. Varescon, "H. Am. Chem. Soc." 103, 3601, 1981 were used thereby as epoxidation agent. For example, chloro-iron (III)-tetraphenyl porphyrin (ClFe(TPP)), chloro-manganese (III)-tetraphenyl porphyrin (ClMn(TPP) or chloro-chromium (III)-tetraphenyl porphyrin (ClCr(TPP)) have been suggested as metal catalysts suitable for reaction with these epoxidation agents. "Manganese (III)-tetraphenyl porphyyrin has also already been used with hydrogen peroxide as oxidation agent (J.-P. Renaud; P. Battioni; J. F. Bartoli; D. Mansuy," J. Chem. Soc., Chem. Commun.", 1985, 888). However, these catalysts exhibit a strong decomposing action on H2O2, so that the selectivities which can be achieved regarding hydrogen peroxide are only very slight unless expensively substituted porphyrin ligands are used.

Oxo-metal porphyrin complexes such as oxo-chloro(5,10,15,20-tetraphenyl porphyrin)-molybdenum (v) (O=Mo (TPP) Cl) have also been suggested heretofore in combination with organic hydroperoxides. However, an attempt to use hydrogen peroxide with a catalyst of the composition oxo(5,10,15,20-tetraphenyl porphyrin)-molybdenum(V) methoxide for epoxidizing the olefin cyclohexene instead of an organic hydroperoxide failed: No epoxidation was able to be observed (F. Varescon, Thesis, Claude Bernard University, Lyons I, 1982).

SUMMARY OF THE INVENTION

In accordance with the present invention, applicants have found that the catalytic epoxidation of olefines with hydrogen peroxide succeeds with very high selectivity in a method wherein the olefin is reacted, either in a homogeneous phase or in a two-phase system, with hydrogen peroxide in the presence of
rhenium-oxo-complexes or
a binuclear compound of the type μ-oxobis [porphyrinatooxorhenium (V)] with
octaethyl porphyrin or
5,10,15,20-tetraphenyl porphyrin or
5,10,15,20-tetra(4-pyridyl)-porphyrin
as ligands in which hydrogen atoms or free electron pairs are optionally substituted one or more times on the phenyl groups or pyridyl groups by halogen, hydroxy, carboxy, cyano, rhodano, nitro, $C_1$–$C_6$-alkyl, trihalogen methyl, $C_1$–$C_6$-alkoxy, $C_1$–$C_6$-alkane sulfonyloxy, aminocarbonyl, aminocarbonyl containing one or two $C_1$–$C_6$-alkyl groups, $C_1$–$C_6$-alkyl carbonyl, amino, di-$C_1$–$C_6$-alkyl amino, $C_1$–$C_6$-alkanoyl amino, $C_1$–$C_6$-alkyl-$C_1$–$C_6$-alkanoyl amino, $C_1$–$C_6$-alkane sulfonyl amino, $C_1$–$C_6$-alkyl-$C_1$–$C_6$-alkane sulfonyl amino, aminosulfonyl, aminosulfonyl containing one or two $C_1$–$C_6$-alkyl groups, $C_1$–$C_6$-alkoxysulfonyl (—SO$_2$—O—$C_1$–$C_6$-alkyl) sulfo or $C_1$–$C_6$-alkane sulfonyl and two of these groups can also be the methylene dioxy group, in which instance the complex in the case of the rhenium-oxo-complexes optionally carries an anion of the series F—, Cl—, Br—, I—, $CH_3O$—, $C_2H_5O$—, $C_3H_7O$—, t—$C_4H_9O$—, $C_6H_5O$—, HO—, AcO—, SCN—, OCN—, $ClO_4$—on the central atom.

In a further aspect of the invention, an organic solvent or a solvent mixture is used as reaction medium for the above described reaction which permits a conversion of hydrogen peroxide added as aqueous solution into the organic phase.

According to another aspect of the invention, when anhydrous hydrogen peroxide is added in the above described reaction, alkyl or cycloalkyl esters of saturated, aliphatic carboxylic acids with a carbon number of 4 to 8 are added as organic solvent for carrying out the method.

Still further, another aspect of the invention involves recovery of the catalyst used for the epoxidation method after separation of the reaction mixture for recycle to further and subsequent epoxidations.

DETAILED DESCRIPTION OF INVENTION

The catalytic properties of the catalysts used in this invention can be controlled and optimized, adapted to the particular olefin, by means of the steric and electronic effects of the mentioned substituents on the phenyl group or pyridyl group of the 5,10,15,20-tetraphenyl porphyrin or 5,10,15,20-tetra-(4-pyridyl) porphyrin.

The catalysts provided in accordance with the present invention for carrying out the method are in part new substances. A number of them are accessible in great purity according to the known methods in the literature: J. W. Buchler et al., "Chem. Ber.", 1973, 106, 2710; "Liebigs Ann. Chem.", 1971, 745, 135; "Inorg. Nucl. Chem. Lett.", 1972, 8, 1073; K. Rohbock, dissertation, RTWH Aachen, 1972; H. Stoppa, dissertation, RTWH Aachen, 1976.

The various porphyrin ligands are prepared, to the extent that they can not be purchased, according to Adler et al., "J. Org. Chem." 32, 476, 1967 and Adler et al., "J. Heterocycl. Chem." 5, 669, 1968 and freed, in so far as required, of chlorine (porphyrin with a partially hydrated pyrrole member) (K. M. Smith et al., "Tetrahedron Lett.", 30,2887, 1973).

The new substances among the rhenium-oxo-complexes described in related application Ser. No. No. 07/247,300 filed Sept. 21, 1988 based on P 37 31 689.3-44 can only be prepared in part according to the known $Re_2O_7$ method.

This related application discloses new methods of preparing these new substances or their precursor for the first time which are also suitable for obtaining the already-known complexes claimed for the method of this invention.

The insertion of rhenium into the optionally substituted porphyrin ligand system succeeds with excess $ReCl_5$ in boiling trichlorobenzene in a very good yield (85–90%) according to equations I and II

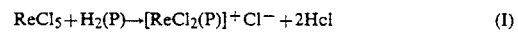

$$ReCl_5 + H_2(P) \rightarrow [ReCl_2(P)]^+ Cl^- + 2Hcl \qquad (I)$$

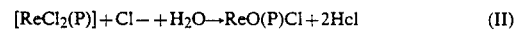

$$[ReCl_2(P)] + Cl^- + H_2O \rightarrow ReO(P)Cl + 2Hcl \qquad (II)$$

The introduction of defined axial ligands as well as the formation of the binuclear complex bridged via oxygen takes place according to equations III and IV.

$$ReO(P)Cl + HX \rightleftharpoons ReO(P)X + HCl \qquad (III)$$

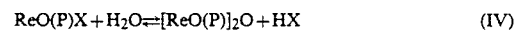

$$ReO(P)X + H_2O \rightleftharpoons [ReO(P)]_2O + HX \qquad (IV)$$

Meanings:
P = porphyrin ligand, optionally substituted;
X = any simply negatively charged anion.

According to the epoxidation method of the present invention, olefines corresponding to the general formula

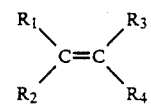

can be reacted, in which $R_1$ to $R_4$ can be identical or different and signify either hydrogen or a linear or branched alkyl group with 1 to 30 carbon atoms or a cycloalkyl group with 3 to 12 C atoms which can contain e.g. one or several O, N or S atoms as heteroatoms.

In the formula, $R_1$ and $R_2$ or $R_3$ and $R_4$ can also be substituted by functional groups which are stable in the reaction environment such as e.g. by hydroxy, chloro, fluoro, bromo, iodo, nitro, methoxy, alkoxy, amino, carbonyl, ester, amido, nitrilo groups. They can also be unsaturated, that is, polyolefins such as e.g. dienes, trienes and other compounds with double bonds can likewise be used in the instant invention whether they are conjugated or not.

Under this condition, among the olefins which can be epoxidized according to the instant method, the following can be considered, for example:

Ethylene, propylene, the butenes, butadiene, the pentenes, isoprene, hexene(1), hexene(3), heptene(1), octene(1), diisobutylene, nonene(1), tetradecene(1) pentamyrcene, camphene, undecene(1), dodecene(1), tridecene(1), tetradecene(1), pentadecene(1), hexadecene(1), heptadecene(1), octadecene(1), nonadecene(1), eicosene(1), the trimers and tetramers of propylene, the polybutadienes, the polyisoprenes, styrene, α-methyl styrene, divinylbenzene, indene, stilbene, cyclopentene, cyclohexene, cycloheptene, cyclooctene, cyclooctadiene, cyclododecene, cyclododecatriene, dicyclopentadiene, methylene cyclopropane, methylene cyclopentane, methylene cyclohexane, vinylcyclohexene, methallyl ketone, allyl chloride, allyl bromide, acrylic acid, methacrylic acid, crotonic acid, vinylacetic acid, crotyl chloride, methallyl chloride, the dichlorobutenes, allyl alcohol, allyl carbonate, allyl acetate, the alkyls of acrylates and methacrylates, diallyl maleate, diallyl phthalate, the unsaturated oils such as soy-bean oil, the unsaturated fatty acids such as oleic acid, linolenic acid, balidic acid, erucic acid, oleostearic acid, myristic acid, palmitin oleic acid, ricinic acid and esters thereof.

An advantage of the invention resides in the fact that the hydrogen peroxide required as reactant can be used hereby in all commercially available forms, for example, in the form of aqueous hydrogen peroxide solutions with a hydrogen peroxide content of 30 to 90 % by wt. or as pure hydrogen peroxide, sharply diluted hydrogen peroxide, anhydrous hydrogen peroxide dissolved in organic solvents or in the form of compounds which release hydrogen peroxide under the reaction conditions (metal peroxides such as magnesium peroxide or zinc peroxide) as well as hydrogen peroxide addition compounds (peroxohydrates), e.g. of sodium carbonate, sodium pyrophosphate and urea.

It is especially advantageous if an organic solvent or an organic solvent mixture is used as reaction medium which permits a conversion of hydrogen peroxide added as aqueous solution into the organic phase.

To this end, alkyl or cycloalkyl esters of saturated, aliphatic carboxylic acids with a carbon number of 4-8 (cf. e.g. DE-PS No. 32 25 307, page 5), methylene chloride, dioxane, tert.-butanol, tetrahydrofurane, benzene, ethanol, chloroform and methanol can be used, for example, as organic solvent.

Potential solvent mixtures are e.g. combinations of one or more of the above-mentioned carboxylic acid esters with water, methylene chloride, dioxane, tert.-butanol, tetrahydrofurane, benzene, ethanol, chloroform and/or methanol. Thus, as the term is used herein "organic solvent" means a single organic solvent, or mixtures of organic solvents, as well as aqueous organic solvents.

An addition of alkyl or cycloalkyl esters of saturated, aliphatic carboxylic acids with a carbon number of 4-8 has proven successful as solvent for the dissolution of anhydrous hydrogen peroxide.

The amounts of catalyst to be used in the method of the invention can fall within a wide range. The catalytic concentration to be used in the individual instance can be selected in accordance with the type of the selected rheniumporphyrin compound provided according to the invention as well as in accordance with the reactivity of the particular olefin to be reacted.

Generally, amounts are in a concentration range of 1/10000 to ½ mole, preferably 1/5000 to 1/5 mole catalyst per mole hydrogen peroxide.

Another feature of the invention is the multiple usage of the catalyst; that is, recycle of catalyst for further batches after suitable separation from the reaction mixture.

The reaction temperatures employed for the method of the invention can be within a wide range. Depending on the particular activity of the catalyst used, the reactivity of the olefin used, the tendency of the desired oxirane to ring opening and the type of solvent, temperatures are generally around 0° to 150°, preferably 20° to 120°, especially 20° to 80° C.

Reaction times can also vary and are normally around 10 minutes to 24 hours.

The reactions can be carried out under atmospheric pressure or at higher pressures as long as the reaction system can be maintained in a liquid phase. The method is preferably performed within a pressure range between 1 and 50 bars.

Among the advantages which can be achieved by carrying out the present invention are:
very short reaction times;
high selectivity (hardly any byproduct);
low catalytic concentration;
high chemical stability of the catalyst, especially in relation to the epoxidation agent;
No or only minimum $H_2O_2$ decomposition;
only water is produced from the epoxidation agent;
catalyst can be easily separated and reused;
simple method.

The invention is described in even more detail in the following with particular reference to the illustrative examples of embodiments.

The catalysts used in the examples of embodiments of the invention obtainable either according to related application Ser. No. 07/247,300 filed Sept. 21, 1988 (No. P 37 31 689.3-44) or according to the cited literature are used for the epoxidation of various olefinic initial substances with hydrogen peroxide according to the invention as follows:

According to version I, a solution of olefin, catalyst and solvent is prepared, heated to a temperature in a range of 20°–100° C. and compounded with hydrogen peroxide (30 to 90 % by wt.).

In accordance with version II a solution of olefin, hydrogen peroxide (30 to 90% by wt.) and solvent is prepared and is then compounded with catalyst; then the reaction is performed under agitation and heating.

In a modified embodiment which can be used equally with versions I and II, a small amount of a heterocyclic amine, e.g. from the family of pyridine or imidazole, is also added to the components in a receiver prior to the addition of the remaining component.

In the case of the olefins added, the reaction can be performed under atmospheric pressure. Specimens are removed in the cours of the reaction and analyzed for their epoxide or $H_2O_2$ content. The amount of epoxides formed is determined either by gas chromatography or titration, that of hydrogen peroxide by means of customary titration with cerium(IV) sulfate. The results obtained in the tests are apparent from the following table in which the selectivity is defined as follows:

$$\text{Selectivity (\%)} = \frac{\text{mole epoxide (diol) formed}}{\text{mole reacted } H_2O_2} \times 100$$

TABLE 1

| Ex. No. | Olefin (mmol) | $H_2O_2$ (mmol) | Catalyst | (mmol) | Solvent | Reacts. conds. Temp. (°C.) | Time (h) | Conv. $H_2O_2$ % | Select. % |
|---|---|---|---|---|---|---|---|---|---|
| 1 | 1,5-COD[(1)] (36) | 85% in $H_2O$ (12) | ORe(TTP)[(3)]OCH$_3$ | $12 \times 10^{-2}$ | nPAC[(2)] | 60 | 6 | 88.7 | 100 |
| 2 | 1,5-COD (36) | 85% in $H_2O$ (12) | ORe(TTP)OCH$_3$* | $12 \times 10^{-2}$ | nPAC | 60 | 2 | 90.3 | 100 |
| 3** | 1,5-COD (36) | — | ORe(TTP)OCH$_3$ | $12 \times 10^{-2}$ | nPAC | 60 | 6 | 0 | 0 |
| 4 | 1,5-COD (18) | 85% in $H_2O$ | ORe(TTP)OCLO$_3$ | $6 \times 10^{-2}$ | nPAC | 60 | 3 | 90.6 | 92.5 |
| 5 | 2-Methyl-2-butene (36) | 85% in $H_2O$ (12) | ORe(TTP)OCH$_3$ | $12 \times 10^{-2}$ | nPAC | 60 | 6 | 68.1 | 84.3 |
| 6 | 1,5-COD (9) | 85% in $H_2O$ (3) | ORe(TTP)OAc | $3 \times 10^{-2}$ | nPAC | 60 | 2 | 63.9 | 71.6 |
| 7 | Cyclohexene (36) | 85% in $H_2O$ (12) | ORe(TTP)OCH$_3$ | $12 \times 10^{-2}$ | tert.-Butanol | 60 | 6 | 98.5 | 68.0 |

[(1)]1,5-Cyclooctadiene
[(2)]acetic acid propyl ester
[(3)]TTP = 5,10,15,20-Tetra (p-tolyl)-porphyrin
[(4)]TTP = 5,10,15,20-Tetraphenylporphyrin
*recycle of catalyst of ex. 1
**control ex.

TABLE 2

| Ex. No. | Olefin (mmol) | $H_2O_2$ (mmol) | Catalyst | (mmol) | Solvent | Reacts. conds. Temp. (°C.) | Time (h) | Conv. $H_2O_2$ % | Select. % |
|---|---|---|---|---|---|---|---|---|---|
| 8 | Cyclohexene (30) | 85% in $H_2O$ (10) | ORe(TTP)[(1)]Br | 0.10 | tert.But. | 60 | 6 | 70.0 | 82.9 |
| 9 | 1,5-COD[(2)] (18) | 85% in $H_2O$ (6) | ORe(TPP)$_2$[(3)]O[(4)] | 0.06 | nPAC[(5)] | 60 | 6 | 84.3 | 56.5 |
| 10 | Cyclohexene (36) | 85% in $H_2O$ (12) | ORe(TAP)[(6)]OCH$_3$ | 0.12 | tert.But. | 60 | 6 | 93.6 | 34.6 |
| 11 | Cyclohexene (36) | 85% in $H_2O$ (12) | ORe(TpCP)[(7)]OCH$_3$ | 0.12 | tert.But. | 60 | 6 | 67.2 | 73.9 |
| 12 | Cyclohexene (36) | 85% in $H_2O$ (12) | ORe(TAP)OCH$_3$* | 0.12 | tert.But. | 60 | 6 | 53.2 | 52.8 |

[(2)]1,5-Cyclooctadiene
[(5)]acetic acid n-propyl ester
[(1)]TTP = 5,10,15,20,-Tetra (p-tolyl)-porphyrin
[(3)]TPP = 5,10,15,20-Tetraphenylporphyrin
[(4)]u-Oxobis[porphyrinatooxorhenium(V)]
[(6)]TAP = 5,10,15,20-Tetraanixylporphyrin
[(7)]TcCP = 5,10,15,20-Tetra(p-chlorphenylporphyrin
*recycle of catalyst of Example 10

Further variations and modification will apparent to those skilled in the art from the foregoing and are intended to be encompassed by the claims appended hereto. German priority application No. P 37 31 690.7-42 is relied on and incorporated herein.

We claim:

1. A method for the catalytic epoxidation of olefins with hydrogen peroxide, comprising reacting an olefin in a homogeneous phase or in a two-phase system with a source of hydrogen peroxide in the presence of rhenium-oxo-complexes or
   a binuclear compound of the type μ-oxobis [porphyrinatooxorhenium (V)]with
   octaethyl porphyrin or
   5,10,15,20-tetraphenyl porphyrin or
   5,10,15,20-tetra(4-pyridyl)-porphyrin
as ligands in which hydrogen atoms or free electron pairs are optionally substituted once or several times on the phenyl groups or pyridyl groups by halogen, hydroxy, carboxy, cyano, rhodano, nitro, $C_1$-$C_6$-alkyl, trihalogen methyl, $C_1$-$C_6$-alkoxy, $C_1$-$C_6$-alkane sulfonyloxy, aminocarbonyl, aminocarbonyl containing one or two $C_1$-$C_6$-alkyl groups, $C_1$-$C_6$-alkyl carbonyl, amino, di-$C_1$-$C_6$-alkyl amino, $C_1$-$C_6$-alkanoyl amino, $C_1$-$C_6$-alkyl-$C_1$-$C_6$-alkanoyl amino, $C_1$-$C_6$-alkane sulfonyl amino, $C_1$-$C_6$-alkyl-$C_1$-$C_6$-alkane sulfonyl amino, aminosulfonyl, aminosulfonyl containing one or two $C_1$-$C_6$-alkyl groups, $C_1$-$C_6$-alkoxysulfonyl (—SO$_2$—O—$C_1$-$C_6$-alkyl) sulfo or $C_1$-$C_6$-alkane sulfonyl and two of these groups can also be the methylene dioxy group, in which instance the complex in the case of the rhenium-oxo-complexes optionally carries an anion of the series F—, Cl—, Br—, I—, CH$_3$O—, C$_2$H$_5$O—, C$_3$H$_7$O—, t—C$_4$H$_9$O—, C$_6$H$_5$O—, HO—, AcO—, SCN—, OCN—, ClO$_4$— on the central atom.

2. The method according to claim 1, wherein organic solvent is used as reaction medium which permits a conversion of hydrogen peroxide added as aqueous solution into the organic phase.

3. The method according to claim 1, further comprising when anhydrous hydrogen peroxide is added to the reaction medium, alkyl or cycloalkyl esters of saturated, aliphatic carboxylic acids with a carbon number of 4 to 8 are added as organic solvent.

4. The method according to claim 1, wherein the catalyst used for the reaction is recycled after separation of the reaction mixture for further epoxidations.

5. The method according to claim 1 wherein the amount of catalyst used in 1/10000 to ½ mole catalyst per mole of hydrogen peroxide.

6. The method according to claim 1 wherein the temperature of reaction is 0° to 150° C.

7. The method according to claim 1 wherein the time of reaction is 10 minutes to 24 hours.

8. The method according to claim 1 wherein the olefin, catalyst and organic solvent are mixed together, heated and then reacted with hydrogen peroxide.

9. The method according to claim 1 wherein the olefin, hydrogen peroxide and solvent are mixed together and thereafter the catalyst is mixed therewith and the resulting reaction mixture is heated to the temperature of reaction.

10. The method according to claim 1 wherein reaction temperature is 20° to 120° C.

11. The method according to claim 1 wherein reaction temperature is 20° to 80° C.

12. The method according to claim 1 wherein the catalyst is a mono-rhenium complex with 5,10,15,20-tetraphenyl porphyrin.

13. The method according to claim 12 wherein said porphyrin is substituted on at least one phenyl group with $C_1$-$C_6$-alkyl as a substituent.

* * * * *